United States Patent
Wang et al.

(10) Patent No.: US 11,648,136 B2
(45) Date of Patent: May 16, 2023

(54) VASCULAR STENT WITH A MIXED CONFIGURATION OF CONNECTORS

(71) Applicant: Biosensors International Group, Ltd., Hamilton (BM)

(72) Inventors: Dan Wang, Singapore (SG); Koon Kiat Teu, Singapore (SG); Debashis Dutta, Irvine, CA (US); John Shulze, Singapore (SG)

(73) Assignee: Biosensors International Group, Ltd., Hamilton (BM)

(*) Notice: Subject to any disclaimer, the term of this patent is extended or adjusted under 35 U.S.C. 154(b) by 348 days.

(21) Appl. No.: 16/738,901

(22) Filed: Jan. 9, 2020

(65) Prior Publication Data

US 2020/0253758 A1 Aug. 13, 2020

Related U.S. Application Data (62) Division of application No. 14/307,723, filed on Jun. 18, 2014, now Pat. No. 10,548,749.

(60) Provisional application No. 61/837,553, filed on Jun. 20, 2013.

(51) Int. Cl.
| | | |
|---|---|---|
| A61F 2/90 | (2013.01) | |
| A61L 31/02 | (2006.01) | |
| A61F 2/915 | (2013.01) | |
| A61L 31/16 | (2006.01) | |

(52) U.S. Cl.
CPC ............. *A61F 2/90* (2013.01); *A61F 2/915* (2013.01); *A61L 31/022* (2013.01); *A61L 31/16* (2013.01); *A61F 2002/91541* (2013.01); *A61F 2002/91575* (2013.01); *A61F 2240/001* (2013.01); *A61L 2300/416* (2013.01); *Y10T 29/49* (2015.01)

(58) Field of Classification Search
CPC . A61F 2/90; A61F 2/915; A61L 31/02; A61L 31/16
See application file for complete search history.

(56) References Cited

U.S. PATENT DOCUMENTS

| | | | |
|---|---|---|---|
| 5,133,732 | A | 7/1992 | Wiktor |
| 5,292,331 | A | 3/1994 | Boneau |
| 5,843,175 | A | 12/1998 | Frantzen |
| 6,071,308 | A | 6/2000 | Ballou et al. |
| 6,331,189 | B1 | 12/2001 | Wolinsky et al. |

(Continued)

FOREIGN PATENT DOCUMENTS

| | | |
|---|---|---|
| CN | 102740806 | 10/2012 |
| EP | 1477130 | 11/2004 |

(Continued)

OTHER PUBLICATIONS

Application No. CN201480045953.8, Office Action, dated Nov. 25, 2016, 12 pages.

(Continued)

*Primary Examiner* — Matthew W Schall
(74) *Attorney, Agent, or Firm* — Kilpatrick Townsend and Stockton LLP (57) ABSTRACT

This invention provides for a radially expandable stent having superior strength and reduced foreshortening properties. The stents have a mixed configuration of straight and (Continued)

arcuate connector segments that serve to join annular segments that make up the body of the stent. Surprisingly the described mixed configuration provides superior resistance to flip deformation while maintaining desired flexibility.

12 Claims, 3 Drawing Sheets (56) References Cited

U.S. PATENT DOCUMENTS

| | | | |
|---|---|---|---|
| 6,565,602 B2 | 5/2003 | Rolando et al. |
| 6,730,117 B1 | 5/2004 | Tseng et al. |
| 6,786,922 B2 | 9/2004 | Schaeffer |
| 6,818,013 B2 | 11/2004 | Mitelberg et al. |
| 6,896,697 B1 | 5/2005 | Yip et al. |
| 6,896,698 B2 | 5/2005 | Rolando et al. |
| 7,329,276 B2 | 2/2008 | Smith et al. |
| 7,331,987 B1 | 2/2008 | Cox |
| 7,578,840 B2 | 8/2009 | Schaeffer |
| 7,637,939 B2 | 12/2009 | Tischler |
| 7,686,843 B2 | 3/2010 | Moore |
| 8,152,842 B2 | 4/2012 | Schlun |
| 8,257,424 B2 | 9/2012 | Orlowski |
| 2002/0173839 A1 | 11/2002 | Leopold et al. |
| 2003/0199969 A1 | 10/2003 | Steinke et al. |
| 2005/0080479 A1 | 4/2005 | Feng et al. |
| 2005/0149168 A1 | 7/2005 | Gregorich |
| 2005/0222671 A1 | 10/2005 | Schaeffer et al. |
| 2006/0004437 A1 | 1/2006 | Jayaraman |
| 2006/0190072 A1 | 8/2006 | Das |
| 2006/0276880 A1 | 12/2006 | Neuss et al. |
| 2008/0065195 A1 | 3/2008 | Brown et al. |
| 2008/0114450 A1 | 5/2008 | Smith et al. |
| 2008/0119925 A1 | 5/2008 | Yadin |
| 2008/0132995 A1 | 6/2008 | Burgermeister et al. |
| 2011/0190871 A1 | 8/2011 | Trollsas et al. |

FOREIGN PATENT DOCUMENTS

| | | |
|---|---|---|
| JP | 2008546484 | 12/2008 |
| JP | 2012517247 | 8/2012 |
| WO | 0071053 | 11/2000 |
| WO | 0121101 | 3/2001 |

OTHER PUBLICATIONS

Application No. EP14814637.6, Extended European Search Report, dated Dec. 5, 2016, 9 pages.
Application No. JP2016-521552, Office Action, dated May 29, 2018, 10 pages.
Application No. JP2016-521552, Office Action, dated Jan. 17, 2019, 13 pages.
Pant et al., "The Influence of Strut-Connectors in Stented Vessels: a Comparison of Pulsatile Flow Through Five Coronary Stents", Annals of Biomedical Engineering, vol. 38, No. 5, May 2010, pp. 1893-1907.
Application No. PCT/US2014/043018, International Search Report and Written Opinion, dated Nov. 5, 2014, 10 pages.
Application No. SG11201510447P, Written Opinion, dated Oct. 10, 2017, 6 pages.
Application No. SG11201510447P, Written Opinion, dated Sep. 21, 2016, 7 pages.

Figure 2, A and B

VASCULAR STENT WITH A MIXED CONFIGURATION OF CONNECTORS

This application is a U.S. Divisional Application of Ser. No. 14/307,723, filed Jun. 18, 2014, which is a U.S. Non-Provisional of U.S. Provisional Application No. 61/837,553, filed Jun. 20, 2013, the disclosures of which are incorporated herein in their entireties for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

This invention provides for a radially expandable stent having superior strength and reduced foreshortening properties. The stents have a mixed configuration of straight and arcuate connector segments that serve to join annular segments that make up the body of the stent. Surprisingly the described mixed configuration provides superior resistance to flip deformation while maintaining desired flexibility.

BACKGROUND OF THE INVENTION

This invention provides for a radially expandable stent having superior strength and reduced foreshortening properties. The stents have a mixed configuration of straight and arcuate connector segments that serve to join annular segments that make up the body of the stent. Surprisingly, the described mixed configuration with three links provides superior resistance to flip deformation and longitudinal compression while maintaining desired flexibility.

BRIEF SUMMARY OF THE INVENTION

This invention provides for a radially expandable stent for insertion into a body vessel having a tubular body with distal and proximal ends, the tubular body comprising: a plurality of annular segments defining a longitudinal axis where each annular segment has a substantially zig-zag shape forming a series of peaks and valleys wherein the plurality of annular segments comprise a distal and a proximal annular end segment respectively defining the distal and proximal ends of the tubular body and at least two annular segments positioned internally between the two end annular segments; and, a plurality of connector segments positioned parallel to the longitudinal axis and bridging the annular segments where the connector segments between the end segments and their adjoining internal segments are straight, are at least three in number, and at least 90% of the connector segments between the internal annular segments are arcuate.

The stents may further comprise a configuration where the peaks and valleys of the annular segments are 180° out of phase with the annular segment adjacent to it such that the peaks of a first and a third annular segment extend toward a second annular segment positioned between the first and third segments and are aligned longitudinally with the valleys of the second annular segment. Alternatively, the stents may be configured such that the peaks and valleys of the annular segments are in phase with the annular segment adjacent to it such that the peaks of a first and a third annular segment extend toward a second annular segment positioned between the first and third segments and are aligned longitudinally with the peaks of the second annular segment.

Further, the stents of this invention may be configured such that the connector segments between the distal annular end segment and the next two internally positioned annular segments are straight.

It is preferred that the straight connector segments between annular end segments and their adjoining annular internal segments are three in number and they may optionally be positioned equidistant from each other along the circumference of the tubular body.

It is preferred that the stents described herein have a flip force required to catastrophically deform the stent of greater than 0.2 newtons.

The stents described herein may be formed of a metal tubular body such as a cobalt chromium alloy.

The stents described herein may further comprise a drug-eluting coating. The coating may comprise rapamycin or a 40-0 derivative of rapamycin.

In addition, this invention provides for a method of manufacturing a radially expandable stent for insertion into a body vessel having the above-described configurations and properties.

BRIEF DESCRIPTION OF THE DRAWINGS

FIG. 1A is a flatten perspective. FIG. 1B is a circular perspective. FIG. 1C is a head on perspective.

FIG. 2(a) is the modified tensile tester. FIG. 2(b) is the needle prior to stent deformation; and, FIG. 2(c) is after stent deformation.

DETAILED DESCRIPTION OF THE INVENTION

This invention provides an improved stent design that enhances a stent's radial stiffness, decreases undesired foreshortening, and allows for necessary longitudinal flexibility. The improvement being a mixed configuration of connectors linking stent segments. More particularly, the stents of this invention provide for improved mechanical strength of stents and are solving the problem of stent distortion that can happen at either end of the stent during deployment. Stent distortions can happen at both distal and proximal ends. When a stent is tracked through the arterial system it can encounter external obstacles, such as lesions, and there is a tendency for the crowns at either ends to distort or to flip. The resistance to flip is mainly dependent on the stent design and its material. Proximal end damage is especially common after the stent is expanded and the physician tries to cross the stent with a guidewire or hits the stent with a guide catheter. Recovery of a distorted stent may require emergency surgery.

In addition, this invention provides for stents with improved radial stiffness. Radial stiffness is the effectiveness of the stent in resisting diameter loss due to vessel recoil and other mechanical events. Radial stiffness is defined as the hoop force per unit length required to elastically change stent diameter.

The stents of this invention also have less foreshortening than prior art stents with uniform configurations of connectors. Foreshortening refers to the fact that the expansion of the stent or its opening results in geometric shortening of the stent. Foreshortening is defined as $L-L_{load}/L$ where L is length pre load and $L_{load}$ is length after expansion. Foreshortening can lead to large inaccuracies and is a known issue in stent design. There are a number of solutions to this problem. See for example: U.S. Pat. No. 6,761,731 entitled, "Balloon-Stent Interaction To Help Reduce Foreshortening" and US Pat. Publ. No. 2003/0105517 entitled: "Non-foreshortening Stent."

Mechanical Design

The stent bodies of this invention are made of a biocompatible material. These materials include cobalt chromium, nickel, magnesium, tantalum, titanium, stainless steel, nitinol, gold, platinum, inconel, iridium, silver, tungsten, and/or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; poly-L-lactic acid, poly-DL-lactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these.

In general, the stents of this invention include an expandable stent body (1) formed of interconnected filaments. The filaments form radial segments (2) joined to each other by connector segments or linkers (3). The connector segments or linkers (3) are straight or arcuate. The straight connector segments are placed between the end radial segments (2) defining the proximal and distal ends of the stents. The radial segments (2) internal to the proximal and distal radial segments are connected to each other by arcuate connector segments (3). The radial segments (2) can have an expandable zig-zag, sawtooth, helical ribbon coil or sinusoidal wave structure, and the connector segments can be in line with each other or staggered.

Figure 1:
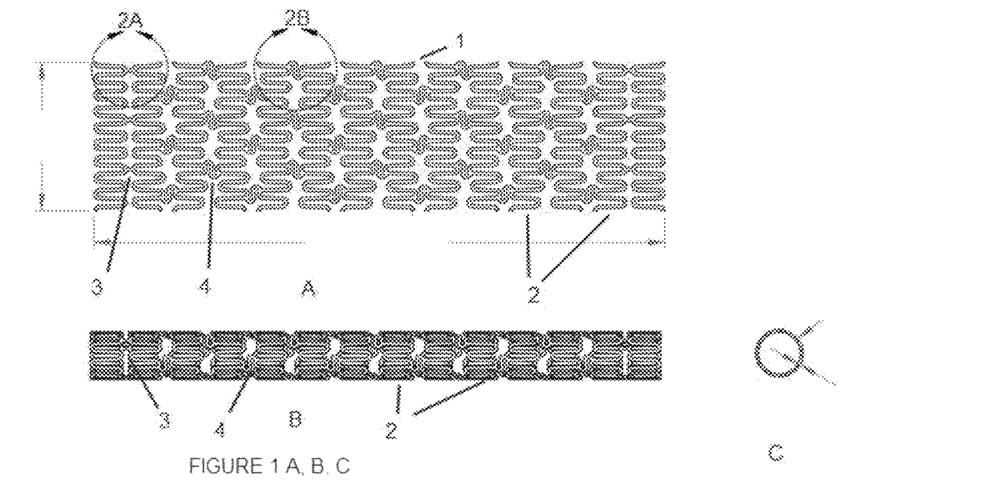
FIG. 1 (A-C) provides an overview of a cobalt chromium stent of this invention with three connector segments per annular ring.
Figure 2:
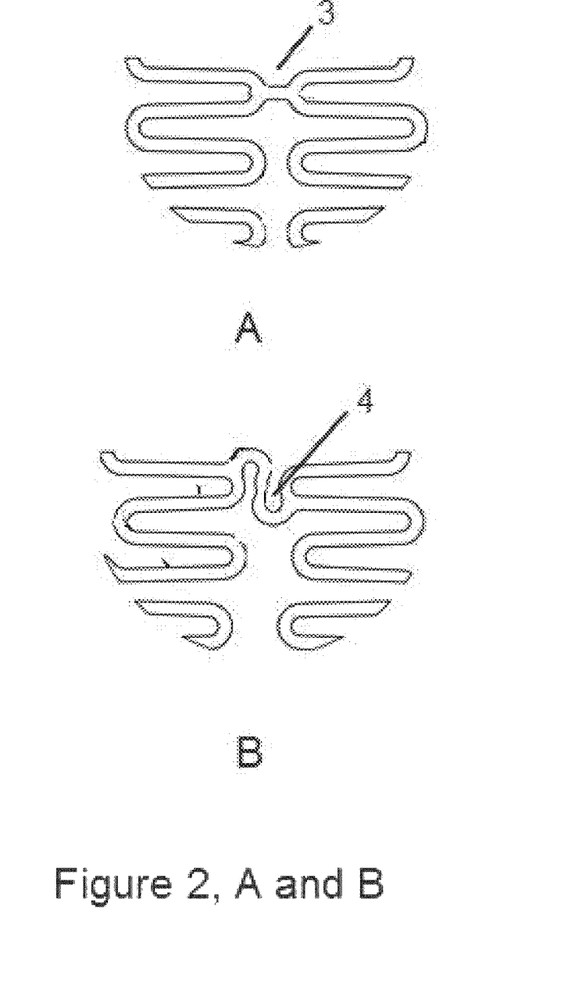
FIGS. 2 (A and B) provides an enlargement of the connectors in FIG. 1 with FIG. 2A illustrating the straight connector and FIG. 1B illustrating the arcuate connector.

The connector segments are generally between 0.1 mm and 0.5 mm. See FIGS. 1 and 2. The number and spacing of the connectors (3,4) affects the mechanical performance of the stent. There can be any number of connector segments between the radial segments (4); but, typically there are between 2 and 6 evenly spaced around the radius of the stent. They can be in either an in line or in a staggered arrangement relative to each other. Depending on the length and desired flexibility, the straight connectors may be used between the first pair of annular segments internal to the distal and proximal ends of the stent.

The contracted-state diameter of the stent is between approximately 0.5 mm to 2.0 mm, preferably 0.71 to 1.65 mm, and a length of between 5 to 100 mm. The expanded stent diameter is at least twice and up to 8-9 times that of the stent in its contracted state, for example, a stent with a contracted diameter of between 0.7 to 1.5 mm may expand radially to a selected expanded state of between 2.0 to 8.0 mm or more. Stents having this general stent-body architecture of linked, expandable tubular members are known, for example, as described in PCT Publication No. WO 99/07308, which is commonly owned with the present application and expressly incorporated by reference herein.

The dimensions of a stent will vary depending on the body lumen in which they are to be delivered. For example, a stent may have a diameter ranging from approximately 0.5 mm to approximately 25.0 mm, and a length that ranges from approximately 4 mm to approximately 100 mm, 200 mm or longer. Stents intended for use in coronary vasculature are typically 1.5 mm to 6 mm in diameter, and from 5 mm to 60 mm long. Stents intended for peripheral vasculature can range from 1.5 mm to 12 mm in diameter and from 5 mm to 200 mm in length. An example of coronary stent measurements is described in co-owned U.S. Pat. No. 6,939,376, which is commonly owned and expressly incorporated by reference herein.

Manufacture

The technological aspects for manufacturing stents of this invention are well known and not critical to the understanding of implementation of the invention. In general terms, the stents are simply bodies with tubular envelopes having walls with openings. Three basic approaches are used to manufacture the stents. One can form the stent from a continuous tubular blank cut up into individual stents. The opening in the walls forming the filaments formed by techniques such as laser cutting, photo-engraving, electron-discharge, machining, etc. Alternatively, the stents may be produced from a strip-like body in which the regions with openings are formed, for example, by the techniques mentioned above, with a view to the subsequent closure of the strip-like element to form a tube, and lastly, the stents can be formed from a metal wire shaped by the successive connection of loops of wire, for example, by means of micro-welding, brazing, gluing, crimping operations, etc.

The first solution described above is currently preferred for producing stents according to the embodiments described herein. In particular, laser-beam cutting has been found the most flexible solution with regard to the ability to form the recited characteristics of the stents. Commercially available stent laser cutting machines are available. See for example: TLS-HT1100 from THETA Kunshan Theta Micro Co, Ltd, PR China and SCS 100 DH from Trotec located in Austria, Rofin (Germany).

For stents fabricated from Nitinol, the pattern of the stent and connecting is programmed into a computer-guided laser cutter or lathe. The lathe cuts into a Nitinol tube into filaments of radial segments and connecting segments in a manner which closely controls the outside diameter and wall thickness of the stent. After the cutting step, the nitinol stent is progressively expanded until it reaches its fully expanded state. The expansion can be performed by an internal expansion fixture, although other expansion apparatus and methods can be used. Once expanded to its fully expanded state, the stent is heat-treated to "set" the shape memory of the Nitinol material to the fully expanded dimensions, then cleaned and electro-polished.

The stent is then compressed into a dimension which allows for delivery into a vessel, either through percutaneous delivery or through minimally invasive surgical procedures. Specifically, the stent is compressed into a smaller state so that it can be delivered by a delivery device to the desired location of the vessel. Any conventional delivery device could be used, such as but not limited to a tube, catheter, or sheath. The compression is accomplished at low temperatures and involves radial and longitudinal compression to maintain the desired (same) length. This compression is accomplished by cooling the stent 40 to a low temperature, for example, zero degrees Celcius, and while maintaining this temperature, compressing the stent to allow the stent to be inserted inside the delivery device. Once inserted inside the delivery device, the stent is held by the delivery device in the compressed state at room temperature.

A textured stent surface is often desired. See U.S. Pat. No. 6,805,898. In one embodiment, the method includes use of a mask to prevent at least a portion of the stent from being abraded. Preferably, the mask is a hydrocarbon film, such as PARAFILM®, however, it will be appreciated that any suitable barrier to abrasion is suitable for use in these methods.

Accordingly, in a preferred embodiment, at least the luminal surface of the stent is not abraded or textured. In one embodiment, a sheet of the mask approximately 5 mm by 60 mm is rolled around the diameter of a mandrel such as a 1.4 mm glass capillary tube. The stent is positioned onto the mandrel and hand-crimped into the hydrocarbon mask. A stereo microscope set between 10× and 40× may be used to ensure that the portion of the stent that is not to be abraded is covered by the mask. In a preferred embodiment, at least 80% of the stent wall thickness on all surfaces is masked by the hydrocarbon film layer. In one embodiment, the stent surface 5 is then treated by utilizing microblasting systems, such as the MICRO BLASTER® and PROCENTER® by Comco, Inc. or an equivalent.

In one embodiment, 25 μm of an abrasive, such as aluminum oxide, is used to roughen the stent surface. The pressure is adjusted to 40 psi±5 psi, and a spray nozzle is positioned approximately 2.5 μm to 5.0 μm from the stent surface, making multiple passes over the stent. In another embodiment, the mask is removed by any appropriate means such as with a solvent or via ultrasonic cleaning.

Due to the roughening of the stent surface, different elements may be expressed on the metal surface which can increase the susceptibility to corrosion. As a result, the treated stent is generally passivated according to 30 ASTM standards and cleaned in a series of solvents such as chloroform, acetone, and/or isopropyl alcohol.

In another embodiment, the surface of the stent is uniformly abraded in a controlled manner via shot peening. Roughening of a stent surface is accomplished using metal particles called shot that range in size from approximately 1 to 5 microns and is made from an atomic element having at least a weight of 43 g/mol. For example, the shot may be in the form of particulate tantalum, particulate tungsten, particulate platinum, particulate iridium, particulate gold, particulate bismuth, particulate barium.

A preferred texture is characterized by a surface roughness of at least about 20 μin (0.5 μm), and a surface roughness range of between about 300-700 82 in (7.5-17.5 μm). Carried on the roughened regions of the stent filaments is a polymer-free coating of a limus drug having a coating thickness greater than the range of surface roughness of the roughened stent surface.

While certain methods of manufacture have been described above, it will be appreciated by those skilled in the art that other methods of manufacture can be utilized without departing from the spirit and scope of the present invention.

Drug Coatings

Stents of this invention may be coated with a polymer or with a therapeutic substance or with a polymer containing one or more therapeutic substances known to one of ordinary skill in the art. One or more therapeutic substances can be added to the stents of this invention by dissolving or mixing the therapeutic substances in a solvent and applying the therapeutic substance and solvent mixture to the surface of the stent. The coating may be abluminal or conformal.

In general, coating a stent with a polymer containing the therapeutic substance requires that a solution of the polymeric material and one or more therapeutic substances are mixed, often with a solvent, and the polymer mixture is applied to the stent. Examples of suitable first solvents include, but are not limited to, acetone, ethanol, methanol, isopropanol, tetrahydrofuran, and ethyl acetate.

The preferred polymers used for coatings are film-forming polymers that have molecular weight high enough as to not be waxy or tacky. The polymers also must adhere to the stent and not be so readily deformable after deposition on the stent as to be able to be displaced by hemodynamic stresses. The polymers' molecular weight must be high enough to provide sufficient toughness so that the polymers will not to be rubbed off during handling or deployment of the stent and must not crack during expansion of the stent. The melting point of the polymer used in the present invention should have a melting temperature of at least 40° C. and preferably above 50° C.

An implantable device may also be top coated with a polymer which does not contain a therapeutic substance, for example, to form a sealant layer over an underlying layer, which does contain a therapeutic substance.

The polymer of choice depends on the desired rate of release or the desired degree of polymer stability. The polymer used for coating may be bioabsorbable or biostable. A bioabsorbable polymer bio-degrades or breaks down in the body and is not present sufficiently long after implantation to cause an adverse local response. Bioabsorbable polymers are gradually absorbed or eliminated by the body by hydrolysis, metabolic process, bulk, or surface erosion. A bioabsorbable polymer is often preferred due to a reduction in the possibility of any chronic local response or separation of polymer from stent.

Examples of bioabsorbable, biodegradable materials include but are not limited to: aliphatic polyesters, copoly (ether-esters), polyalkylenes oxalates, polyamides, poly (iminocarbonates), polyorthoesters, polyoxaesters, polyamidoesters, polyoxaesters containing amido groups, poly (anhydrides), polyphosphazenes, biomolecules and blends thereof.

Copoly(ether-esters) for the purpose of this invention include those copolyester-ethers described in Journal of Biomaterials Research, Vol. 22, pages 993-1009, 1988 by Cohn and Younes and Cohn, Polymer Preprints (ACS Division of Polymer Chemistry) Vol. 30(1), page 498, 1989 (e.g. PEO/PLA).

Aliphatic polyesters include homopolymers and copolymers of lactide (which includes lactic acid d-,l- and meso lactide), ε-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one and polymer blends thereof.

Polyalkylene oxalates for the purpose of this invention include U.S. Pat. Nos. 4,208,511; 4,141,087; 4,130,639; 4,140,678; 4,105,034; and 4,205,399 (incorporated by reference herein).

Polyphosphazenes, co-, ter- and higher order mixed monomer based polymers made from L-lactide, D,L-lactide, lactic acid, glycolide, glycolic acid, para-dioxanone, trimethylene carbonate and .epsilon.-caprolactone such as are described by Allcock in The Encyclopedia of Polymer Science, Vol. 13, pages 31-41, Wiley Intersciences, John Wiley & Sons, 1988 and by Vandorpe, Schacht, Dejardin and Lemmouchi in the Handbook of Biodegradable Polymers, edited by Domb, Kost and Wisemen, Hardwood Academic Press, 1997, pages 161-182 (which are hereby incorporated by reference herein).

Poly(iminocarbonate) for the purpose of this invention include as described by Kemnitzer and Kohn, in the Handbook of Biodegradable Polymers, edited by Domb, Kost and Wisemen, Hardwood Academic Press, 1997, pages 251-272.

Polyanhydrides from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons.

Polyoxaesters, polyoxaamides and polyoxaesters containing amines and/or amido groups are described in a mini review by Andejelic et al., (2007) The Polyoxaesters in Polymer International 56(9):1063-1077 and in the following U.S. Pat. Nos. 5,464,929; 5,595,751; 5,597,579; 5,607,687; 5,618,552; 5,620,698; 5,645,850; 5,648,088; 5,698,213 and 5,700,583 incorporated herein by reference.

Polyorthoesters of use in this invention are those described by Heller in Handbook of Biodegradable Polymers, edited by Domb, Kost and Wisemen, Hardwood Academic Press, 1997, pages 99-118 (hereby incorporated herein by reference).

Film-forming polymeric biomolecules for the purpose of this invention include naturally occurring materials that may be enzymatically degraded in the human body or are hydrolytically unstable in the human body such as fibrin, fibrinogen, collagen, elastin, heparin, and absorbable biocompatable polysaccharides such as chitosan, starch, fatty acids (and esters thereof), glucoso-glycans and hyaluronic acid.

Preferred polymer coatings are polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly (glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates.

The preferable coatings to use for this application are bioabsorbable elastomers, more preferably aliphatic polyester elastomers. In the proper proportions aliphatic polyester copolymers are elastomers. Elastomers present the advantage that they tend to adhere well to the metal stents and can withstand significant deformation without cracking. The high elongation and good adhesion provide superior performance to other polymer coatings when the coated stent is expanded.

The preferred bioabsorbable elastomeric polymers should have an inherent viscosity of from about 1.0 dL/g to about 4 dL/g, preferably an inherent viscosity of from about 1.0 dL/g to about 2 dL/g, and most preferably an inherent viscosity of from about 1.2 dL/g to about 2 dL/g as determined at 25° C. in a 0.1 gram per deciliter (g/dL) solution of polymer in hexafluoroisopropanol (HFIP). Mixtures of the fast hydrolyzing and slow hydrolyzing polymers can be used to adjust the time of strength retention.

More specifically, examples of suitable bioabsorbable elastomers are described in U.S. Pat. No. 5,468,253 hereby incorporated by reference. Preferably the bioabsorbable biocompatible elastomers based on aliphatic polyester, including but not limited to those selected from the group consisting of elastomeric copolymers of ε-caprolactone and glycolide (preferably having a mole ratio of ε-caprolactone to glycolide of from about 35:65 to about 65:35, more preferably 45:55 to 35:65); elastomeric copolymers of .epsilon.-caprolactone and lactide, including L-lactide, D-lactide blends thereof or lactic acid copolymers (preferably having a mole ratio of ε-caprolactone to lactide of from about 35:65 to about 90:10, and more preferably from about 35:65 to about 65:35 and most preferably from about 45:55 to 30:70, or from about 90:10 to about 80:20); elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of ε-caprolactone and p-dioxanone (preferably having a mole ratio of ε-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. As is well known in the art, these aliphatic polyester copolymers have different hydrolysis rates, therefore, the choice of elastomer may in part be based on the requirements for the coatings adsorption.

Most preferred are homopolymers of poly D, L-lactic acid, and co-polymers of polylactic acid such as with polyglycolic acid or ε-caprolactone.

Examples of biostable polymers include Parylene®, Parylast®, polyurethane (for example, segmented polyurethanes such as Biospan®)), polyethylene, polyethylene terephthalate, ethylene vinyl acetate, silicone and polyethylene oxide.

Suitable film-forming biostable polymers with relatively low chronic tissue response include polyurethanes, silicones, poly(meth)acrylates, polyesters, polyalkyl oxides (polyethylene oxide), polyvinyl alcohols, polyethylene glycols and polyvinyl pyrrolidone, as well as hydrogels such as those formed from crosslinked polyvinyl pyrrolidinone and polyesters could also be used. Other polymers could also be used if they can be dissolved, cured or polymerized on the stent. These include polyolefins, polyisobutylene and ethylene-alphaolefin copolymers; acrylic polymers (including methacrylate) and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as ethylene-methyl methacrylate copolymers, acrylonitrile-styrene copolymers, ABS resins and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose; cellulose acetate; cellulose acetate; butyrate; cellophane; cellulose nitrate; cellulose propionate; cellulose ethers (i.e. carboxymethyl cellulose and hydroxyalkyl celluloses); and combinations thereof. Polyamides for the purpose of this application would also include polyamides of the form —NH—$(CH_2)_n$—CO— and NH—$(CH_2)_x$—NH—CO—$(CH_2)_y$—CO, wherein n is preferably an integer in the range of from 6 to 13; x is an integer in the range of from 6 to 12;

and y is an integer in the range of from 4 to 16. The list provided above is illustrative but not limiting.

Therapeutic Agents

Therapeutic substances can include, but are not limited to, antineoplastic, antimitotic, antiinflammatory, antiplatelet, anticoagulant, antifibrin, antithrombin, antiproliferative, antibiotic, antioxidant, and antiallergic substances as well as combinations thereof.

Examples of such antineoplastics and/or antimitotics include paclitaxel (e.g., TAXOL® by Bristol-Myers Squibb Co., Stamford, Conn.); docetaxel (e.g., Taxotere® from Aventis S.A., Frankfurt, Germany); methotrexate; azathioprine; vincristine; vinblastine; fluorouracil; doxorubicin hydrochloride (e.g., Adriamycin® from Pharmacia & Upjohn, Peapack N.J.); and mitomycin (e.g., Mutamycin® from Bristol-Myers Squibb Co., Stamford, Conn.).

Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.).

Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide.

Additional antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine). Further, Antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen).

Examples of anticoagulant drugs include heparin, synthetic heparin salts and other inhibitors of thrombin.

Examples of fibrinolytic agents include tissue plasminogen activator, streptokinase and urokinase).

Examples of antiplatelet drugs include aspirin, dipyridamole, ticlopidine, clopidogrel, and abciximab.

Examples of anti-inflammatory drugs include those such as adrenocortical steroids (cortisol, cortisone, fludrocortisone, prednisone, prednisolone, 6.alpha.-methylprednisolone, triamcinolone, betamethasone, and dexamethasone), and non-steroidal agents (salicylic acid derivatives, i.e., aspirin; para-aminophenol derivatives, i.e., acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive: (cyclosporine, tacrolimus (FK-506), sirolimus (rapamycin), azathioprine, mycophenolate mofetil).

In other examples, the therapeutic substance is a radioactive isotope for implantable device usage in radiotherapeutic procedures. Examples of radioactive isotopes include, but are not limited to, phosphoric acid ($H_3P^{32}O_4$), palladium ($Pd^{103}$), cesium ($Cs^{131}$), and iodine ($I^{125}$). While the preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions.

Preferred therapeutic substances are rapamycin derivatives. Most preferred is 42-O-(2-ethoxyethyl) rapamycin (BA9); everolimus and sirolimus.

Methods of applying the therapeutic substance or polymer, or combination of the two, are known to those of skill in the art. Methods include, but are not limited to hand application using a brush, computerized coating devices that directly apply coating from a feed system, physical immersion, spray-coating, sputtering, and gas-phase polymerization.

The solvent is chosen such that there is the proper balance of viscosity, deposition level of the polymer, solubility of the pharmaceutical agent, wetting of the stent, and evaporation rate of the solvent to properly coat the stents. In the preferred embodiment, the solvent is chosen such that the pharmaceutical agent and the polymer are both soluble in the solvent. In some cases, the solvent must be chosen such that the coating polymer is soluble in the solvent and such that pharmaceutical agent is dispersed in the polymer solution in the solvent. In that case, the solvent chosen must be able to suspend small particles of the pharmaceutical agent without causing them to aggregate or agglomerate into collections of particles that would clog the slots of the stent when applied. Although the goal is to dry the solvent completely from the coating during processing, it is a great advantage for the solvent to be non-toxic, non-carcinogenic and environmentally benign. Mixed solvent systems can also be used to control viscosity and evaporation rates. In all cases, the solvent must not react with or inactivate the pharmaceutical agent or react with the coating polymer. Preferred solvents include but are not limited to: acetone, N-methylpyrrolidone (NMP), dimethyl sulfoxide (DMSO), toluene, methylene chloride, chloroform, 1,1,2-trichloroethane (TCE), various freons, dioxane, ethyl acetate, tetrahydrofuran (THF), dimethylformamide (DMF), and dimethylacetamide (DMAC).

The film-forming biocompatible polymer coatings are generally applied to reduce local turbulence in blood flow through the stent, as well as, adverse tissue reactions. The coating may also be used to administer a pharmaceutically active material to the site of the stents placement. Generally, the amount of polymer coating to be placed on the stent will vary with the polymer and the stent design and the desired effect of the coating. As a guideline, the amount of coating may range from about 0.5 to about 20 as a percent of the total weight of the stent after coating and preferably will range from about 1 to about 15 percent. The polymer coatings may be applied in one or more coating steps depending on the amount of polymer to be applied. Different polymers may also be used for different layers in the stent coating. In fact, it is highly advantageous to use a dilute first coating solution as primer to promote adhesion of subsequent coating layers that may contain pharmaceutically active materials.

Additionally, a top coating can be applied to delay release of the pharmaceutical agent, or used as the matrix for the delivery of a different pharmaceutically active material. The amount of top coatings on the stent may vary but will generally be less than about 2000 µg, preferably the amount of top coating will be in the range of about 10 µg to about 1700 µg, and most preferably in the range of from about 300 µg to about 1600 µg. Layering of coating of fast and slow hydrolyzing copolymers can be used to stage release the drug or to control release of different agents placed in different layers. Polymer blends may also be used to control the release rate of different agents or to provide desirable balance of coating (i.e., elasticity, toughness, etc.) and drug delivery characteristics (release profile). Polymers with different solubilities in solvents can be used to build up different polymer layers that may be used to deliver different drugs or control the release profile of a drug. For example, ε-caprolactone-co-lactide elastomers are soluble in ethyl acetate and ε-caprolactone-co-glycolide elastomers are not soluble in ethyl acetate. A first layer of ε-caprolactone-co-glycolide elastomer containing a drug can be over coated with ε-caprolactone-co-glycolide elastomer using a coating solution made with ethyl acetate as the solvent. Additionally, different monomer ratios within a copolymer, polymer structure, or molecular weights may result in different solubilities. For example, 45/55 ε-caprolactone-co-glycolide at room temperature is soluble in acetone, whereas a similar molecular weight copolymer of 35/65 ε-caprolactone-co-glycolide is substantially insoluble within a 4 weight percent solution. The second coating (or multiple additional coatings) can be used as a top coating to delay the drug delivery of the drug contained in the first layer. Alternatively, the second layer could contain a different drug to provide for sequential drug delivery. Multiple layers of different drugs could be provided by alternating layers of first one polymer then the other. As will be readily appreciated by those skilled in the art, numerous layering approaches can be used to provide the desired drug delivery.

Coating may be formulated by mixing one or more therapeutic agents with the coating polymers in a coating mixture. The therapeutic agent may be present as a liquid, a finely divided solid, or any other appropriate physical form. Optionally, the mixture may include one or more additives, e.g., nontoxic auxiliary substances such as diluents, carriers, excipients, stabilizers or the like. Other suitable additives may be formulated with the polymer and pharmaceutically active agent or compound. For example, hydrophilic polymers selected from the previously described lists of biocompatible film forming polymers may be added to a biocompatible hydrophobic coating to modify the release profile (or a hydrophobic polymer may be added to a hydrophilic coating to modify the release profile). One example would be adding a hydrophilic polymer selected from the group consisting of polyethylene oxide, polyvinyl pyrrolidone, polyethylene glycol, carboxylmethyl cellulose, hydroxymethyl cellulose and combination thereof, to an aliphatic polyester coating to modify the release profile. Appropriate relative amounts can be determined by monitoring the in vitro and/or in vivo release profiles for the therapeutic agents.

The best conditions for the coating application are when the polymer and pharmaceutical agent have a common solvent. This provides a wet coating that is a true solution. Less desirable, yet still usable, are coatings that contain the pharmaceutical as a solid dispersion in a solution of the polymer in solvent. Under the dispersion conditions, care must be taken to ensure that the particle size of the dispersed pharmaceutical powder, both the primary powder size and its aggregates and agglomerates, is small enough not to cause an irregular coating surface or to clog the slots of the stent that we need to keep coating-free. In cases where a dispersion is applied to the stent and we want to improve the smoothness of the coating surface or ensure that all particles of the drug are fully encapsulated in the polymer, or in cases where we may want to slow the release rate of the drug, deposited either from dispersion or solution, we can apply a clear (polymer only) top coat of the same polymer used to provide sustained release of the drug or another polymer that further restricts the diffusion of the drug out of the coating. The top coat can be applied by dip coating with mandrel as previously described or by spray coating (loss of coating during spray application is less problematic for the clear topcoat since the costly drug is not included). Dip coating of the top coat can be problematic if the drug is more soluble in the coating solvent than the polymer and the clear coating redissolves previously deposited drug. The time spent in the dip bath may need to be limited so that the drug is not extracted out into the drug-free bath. Drying should be rapid so that the previously deposited drug does not completely diffuse into the topcoat.

The amount of therapeutic agent will be dependent upon the particular drug employed and medical condition being treated. Typically, the amount of drug represents about 0.001% to about 70%, more typically about 0.001% to about 60%, most typically about 0.001% to about 45% by weight of the coating.

The quantity and type of polymers employed in the coating layer containing the pharmaceutical agent will vary depending on the release profile desired and the amount of drug employed. The product may contain blends of the same or different polymers having different molecular weights to provide the desired release profile or consistency to a given formulation.

Absorbable polymers upon contact with body fluids including blood or the like, undergoes gradual degradation (mainly through hydrolysis) with concomitant release of the dispersed drug for a sustained or extended period (as compared to the release from an isotonic saline solution). Non-absorbable and absorbable polymers may release dispersed drug by diffusion. This can result in prolonged delivery (over, say 1 to 2,000 hours, preferably 2 to 800 hours) of effective amounts (say, 0.001 µg/cm$^2$-min to 100 .mu.g/cm$^2$-min) of the drug. The dosage can be tailored to the subject being treated, the severity of the affliction, the judgment of the prescribing physician, and the like.

Individual formulations of drugs and polymers may be tested in appropriate in vitro and in vivo models to achieve the desired drug release profiles. For example, a drug could be formulated with a polymer (or blend), coated on a stent, and placed in an agitated or circulating fluid system (such as PBS 4% bovine albumin). Samples of the circulating fluid could be taken to determine the release profile (such as by HPLC). The release of a pharmaceutical compound from a stent coating into the interior wall of a lumen could be modeled in an appropriate porcine system. The drug release profile could then be monitored by appropriate means such as by taking samples at specific times and assaying the samples for drug concentration (using HPLC to detect drug concentration). Thrombus formation can be modeled in animal models using the $^{111}$In-platelet imaging methods described by Hanson and Harker, Proc. Natl. Acad. Sci. USA 85:3184-3188 (1988). Following this or similar procedures, those skilled in the art will be able to formulate a variety of stent coating formulations.

Deployment

The stent of this invention can be deployed by a number of delivery systems and delivery methods. These delivery systems and methods will vary depending on whether the stent is expanded by self-expansion or radial expansion forces. The methods of the invention are designed to minimize the risk and/or extent of restenosis in a patient who has received localized vascular injury, or who is at risk of vascular occlusion due to the presence of advanced atherosclerotic disease.

Typically the vascular injury is produced during an angiographic procedure to open a partially occluded vessel, such as a coronary or peripheral vascular artery. Alternately, the stent may be introduced into a site of vascular narrowing and expanded using the balloon to directly open up the narrowed portion of the vessel (i.e., the vascular injury disease site). In the first mentioned angiographic procedure, a balloon catheter is first placed at the occlusion site, and a distal-end balloon is inflated and deflated one or more times to force the occluded vessel open. This vessel expansion, particularly involving surface trauma at the vessel wall where plaque may be dislodged, often produces enough localized injury that the vessel responds over time by cell proliferation and reocclusion in the vicinity of the implanted stent. Not surprisingly, the occurrence or severity of restenosis is often related to the extent of vessel stretching involved in the angioplasty procedure.

The present invention is intended to be used without limitations to any particular method of therapeutically treating a vascular site, and can be used with either of the techniques described above, or with alternative techniques for vascular disease and injury as is known. In practicing the present invention, the stent is placed in its contracted state typically at the distal end of a catheter, either within the catheter lumen, or in a contracted state on a distal end balloon. The distal catheter end is then guided to the injury site, or to the site of potential occlusion, and released from the catheter, e.g., by pulling back a sheath covering the stent to release the stent into the site, if the stent is self-expanding, or by expanding the stent on a balloon by balloon inflation, until the stent contacts the vessel walls, in effect, implanting the stent into the tissue wall at the site.

To better view the stent as it travels along the patient's vasculature, radiopaque materials may be included onto or into the stent. These materials include but are not limited to, materials comprising iodine or iodine-derivatives, such as; for example, isohexyl and iopamidol, which are detectable by x-rays.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

Example 1

Fabrication of the New Stent

A stent is fabricated from cobalt-chromium alloy (MP35N). It is laser-cut from cobalt-chromium tubings whose ID varies from 1.2 mm to 1.8 mm. In order to accommodate a wide range of expansion diameters, the stent has either 6 or 9 crowns. The 6-crown stent (SV) can be expanded up to 3.0 mm, and the 9-crown stent (MV) can be expanded up to 4.0 mm, the length of the stent can vary from 9.5 mm to 36.5 mm. Each pattern is comprised of a series of corrugated rings aligned along a common longitudinal axis. Each ring is connected to the adjacent ring by three links/connectors aligned in the longitudinal direction (see FIG. 1). The unique feature of this stent is that the end links are straight, while the rest of the links are serpentine.

Example 2

Figure 3:
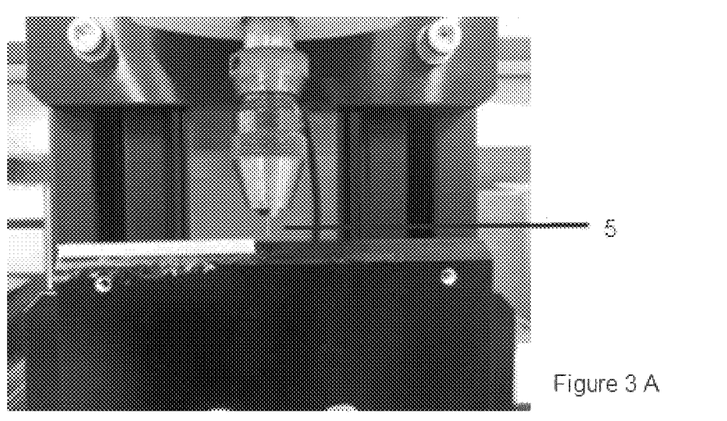
FIGS. 3 (a-c) provide an overview of the tensile tester adapted to test the physical properties of the stents described herein.

A Description of the Flip Force Measurement and Comparison with Stent with Uniform Connectors A new test method was developed to evaluate the resistance to flipping of different stent designs. FIGS. 3 a-c depict the test fixture and test method. The stent was crimped onto a mandrel with the end crown of the stent sticking out from the mandrel. It was placed on a tensile tester and a needle (5) attached to a force gauge was positioned over the exposed crown of the stent. The force required to displace the crown a given distance was used to compare the flip force of the different designs.

It was discovered that the resistance to flipping, and hence, longitudinal distortion, was considerably improved by replacing the end s-links with straight links. The Table below shows the results from the two design iterations. Also, since most of the connectors are still s-links, stent flexibility and tracking was not sacrificed. An increase of 52% in flip/distortion strength was obtained using a stent of Example 1 compared to a stent with three s-shaped connector segments linking the terminal annular segment with an adjacent internal annular segment. See Table 1.

TABLE 1

| Design Rev | Average Flip force (N) |
|---|---|
| Flip force with s-link at the end (Rev 13 results) | 0.150 |
| Flip with straight link at the ends (Rev 16 results) | 0.228 |

Example 3

Minimizing Foreshortening of Stents

Stents tend to foreshorten when expanded from crimped (small diameter) state to larger diameter. The ends of the stents expand first and can push the links inwards in the axial direction—causing stent foreshortening. The problem is exacerbated as stents became more flexible with less axial strength. During the development of the stent of this invention, one unexpected finding was that foreshortening was considerably reduced by incorporating straight links at the end bands and increasing the number of end-links from two to three. The results below show that by combining triple links with straight links at the end, foreshortening can be reduced several folds. See Table 2.

TABLE 2

| Design Rev | Max foreshortening for 9.5 mm stent (%) |
|---|---|
| 2 body link with peak-to-valley design (Rev 16 results) | 13.70 |
| 3 body link with peak-to-peak design (Rev 19 results) | 3.35 |

Example 4

Minimizing Longitudinal Compression of Stents

In addition to foreshortening, longitudinal compression is becoming an increasing issue as stent's become thinner. Longitudinal compression is a distortion that arises when guidewires, catheters and balloons get caught on the edge (proximal to the patient) of the stent during withdrawal procedures or during subsequent interventions.

During the development of the stent of this invention, one unexpected finding was that foreshortening was considerably reduced by incorporating straight links at the end bands. The three straight links resisted deformation during stent expansion and prevented the inner s-links from also collapsing/shortening. The results in Table 1 below were obtained using expanded stents (3 mm) on a mandrel of 2.6 mm diameter. A force of 0.5 newtons was applied to the stents using a donut-shaped component with a lumen of 2.65 mm in a material testing device from Instron (Norwood, Mass.). The Table below compares the longitudinal strength of Element (2 connectors) vs. our current Biomatrix Flex (2 connectors) and with the 'mixed connector design' of this invention. The mixed connector (with 3-link) configuration of this invention gave surprisingly superior resistance to longitudinal compression over the other tested.

| Stent Model (3.0 × 19 mm) | Longitudinal Crush (%) |
|---|---|
| BioMatrix Flex | 28.6 |
| Mixed connector (2-link) | 19.2 |
| Mixed connector (3-link) | 3.0 |
| Xience V | 12.9 |
| Promus Element | 33.8 |
| Resolute Integrity | 17.7 |

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method of manufacturing a radially expandable stent for insertion into a body vessel where the stent has a tubular body with a circumference, a distal end and a proximal end, the method comprising:

forming the tubular body of the stent to have a plurality of annular segments defining a longitudinal axis where each annular segment has a substantially zig-zag shape forming a series of peaks and valleys wherein the plurality of annular segments comprise a distal and a proximal annular end segments respectively defining the distal and proximal ends of the tubular body and at least two annular segments positioned internally between the two end annular segments; and, a plurality of connector segments positioned parallel to the longitudinal axis and bridging the annular segments where the connector segments between the annular end segments and their adjoining internal segments are straight, and are exactly three in number, and at least 90% of the connector segments between the internal annular segments are arcuate.

2. The method of claim 1 wherein the peaks and valleys of the annular segments are 180° out of phase with the annular segment adjacent to it such that the peaks of a first and a third annular segment extend toward a second annular segment positioned between the first and third segments and are aligned longitudinally with the valleys of the second annular segment.

3. The method of claim 1 wherein the straight connector segments between annular end segments and their adjoining annular internal segments are positioned equidistant from each other along the circumference of the tubular body.

4. The method of claim 1 wherein the peaks and valleys of the annular segments are in phase with the annular segment adjacent to it such that the peaks of a first and a third annular segment extend toward a second annular segment positioned between the first and third segments and are aligned longitudinally with the peaks of the second annular segment.

5. The method of claim 1 wherein the connector segments between the distal annular end segment and the next two internally positioned annular segments are straight.

6. The method of claim 1 wherein the flip force required to catastrophically deform the stent is greater than 0.2 newtons.

7. The method of claim 1 where the tubular body is a metal.

8. The method of claim 7 where the metal is a cobalt chromium alloy.

9. The method of claim 1 further comprising a drug eluting coating.

10. The method of claim 1 comprising rapamycin or a 40-O derivative of rapamycin.

11. The method of claim 1, wherein the radially expandable stent has dimensions for supporting a coronary artery.

12. The method of claim 1, wherein the radially expandable stent has dimensions for supporting a peripheral artery.

* * * * *